United States Patent
Vellutato

(10) Patent No.: US 6,607,695 B2
(45) Date of Patent: *Aug. 19, 2003

(54) METHOD OF STERILIZATION

(76) Inventor: Arthur L. Vellutato, 115 Lori Cir., Exton, PA (US) 19341

(*) Notice: Subject to any disclaimer, the term of this patent is extended or adjusted under 35 U.S.C. 154(b) by 2 days.

This patent is subject to a terminal disclaimer.

(21) Appl. No.: 09/994,671

(22) Filed: Nov. 28, 2001

(65) Prior Publication Data

US 2002/0064477 A1 May 30, 2002

Related U.S. Application Data

(63) Continuation of application No. 09/627,398, filed on Jul. 27, 2000, now Pat. No. 6,333,006, which is a continuation of application No. 08/142,049, filed on Oct. 28, 1993, now Pat. No. 6,123,900.

(51) Int. Cl.$^7$ .................................................. A61L 2/00
(52) U.S. Cl. ........................ 422/22; 422/40; 250/455.11
(58) Field of Search ...................... 422/22, 40; 426/521, 426/240; 250/455.11; 206/524.3, 524.2, 524.9; 220/462; 53/167; 99/451

(56) References Cited

U.S. PATENT DOCUMENTS

| | | | |
|---|---|---|---|
| 2,738,429 A | 3/1956 | Goldblith | 422/22 |
| 2,904,392 A | 9/1959 | Pomerantz et al. | 422/22 |
| 2,961,140 A | 11/1960 | Holmes | |
| 3,670,874 A | 6/1972 | Brunner | |
| 3,763,900 A | 10/1973 | Solms-Baruth et al. | |
| 4,065,816 A | * 1/1978 | Sawyer | |
| 4,700,838 A | 10/1987 | Falciani et al. | |
| 4,714,595 A | 12/1987 | Anthony et al. | 422/22 X |
| 4,896,768 A | 1/1990 | Anderson | 422/22 X |
| 4,927,010 A | 5/1990 | Kannankeril | |
| 4,968,624 A | 11/1990 | Bacehowski et al. | |
| 5,060,823 A | 10/1991 | Perlman | |
| 5,518,146 A | 5/1996 | Mattei | |
| 6,123,900 A | 9/2000 | Vellutato | 422/22 |
| 6,333,006 B1 | 12/2001 | Vellutato | 422/22 |

FOREIGN PATENT DOCUMENTS

GB  2 216 422  10/1989

OTHER PUBLICATIONS

Undated excerpts from the Mar. 1992 issue of *Clean Room*. (2 pages).
VAI web page, http://sterile.com/about/aspirations.html, printed Dec. 13, 2000 (1 page).
Undated excerpts from the Mar. 1992 issue of *Clean Rooms Magazine* (3 pages).

* cited by examiner

*Primary Examiner*—Elizabeth McKane
(74) *Attorney, Agent, or Firm*—Blank Rome LLP

(57) ABSTRACT

A sterilized chemical composition is stored in a sterile environment for a prolonged period of time, hermetically sealed in successive enclosures and a shipping enclosure. The third sealing layer is removed prior to entering a storage area. The second layer is removed prior to taking the container to the sterile environment. The storage area may also be sterile. The innermost container may be an aerosol container and the composition a disinfectant liquid such as alcohol. The entire shipping enclosure and contects is preferably sterilized with gamma radiation.

7 Claims, 2 Drawing Sheets

METHOD OF STERILIZATION

This application is a continuation of application Ser. No. 09/627,398 now U.S. Pat. No. 6,333,006 filed on Jul. 27, 2000, which is a continuation of application Ser. No. 08/142,049 now U.S. Pat. No. 6,123,900, filed Oct. 28, 1993.

BACKGROUND OF THE INVENTION

1. Field of the Invention

This invention pertains to methods of optimizing the sterilization process for chemical compositions and to allow extended shelf life for sterilized chemical compositions on-site for operational use. In particular, the subject invention concept is directed to a method of sterilizing chemical compositions utilizing irradiation techniques which allow for the chemical composition being sterilized to be maintained within containers for extended periods of time with the assurance that the contents are maintained in a sterilized state. Still further, this invention concept is directed to an improved sterilization method for chemical compositions in general and particularly for isopropyl alcohol used in decontamination procedures. More particularly, this invention is directed to a method where chemical compositions within containers are hermetically sealed to provide a relatively contaminant free outer surface subsequent to a gamma irradiation process for sterilization of the contents of the container being sealed. Still further, this invention directs itself to a method wherein a hermetically sealed container is further hermetically sealed with a second sealing layer which in itself is formed around and encases the first sealing layer and container. More in particular, this invention directs itself to a method of optimizing the sterilization procedure for a chemical composition by providing a third sealing layer around one or a plurality of double sealed containers prior to a gamma ray irradiation process. Still further, this invention provides for a series of processing steps whereby a carton containing sterilized containers may be shipped to a relatively contaminated area and removed to a relatively contamination free area while still maintaining a double hermetic seal around the sterilized containers.

2. Prior Art

Sterilization procedures for chemical compositions are well known in the art. However, increasing statutory demands call for extended, complicated and time-consuming sterilization procedures which require detailed cataloguing and analysis associated with the assurance that a sterilized composition is being maintained in a sterilized state over a period of time so that such can be assured of being sterilized when operationally used.

In some prior art techniques, a single covering layer is used for sealing irradiated chemical compositions. However, such sterilized chemical compositions lose their sterilization ratings over an extended period of time due to the fact that even when on the shelf of a clean room, such are impinged with various microorganisms and contamination particulates. Thus, shelf lives had to be catalogued with the result that there was extended periods of time used in documenting as well as analyzing sterilization procedures in maintaining the sterilization requirements. Still further, in other prior art systems, the contents of a container were irradiated however, no sealing layers were added which even further decreased the sterilization maintenance of the contained chemical compositions.

SUMMARY OF THE INVENTION

This invention is directed to a method of sterilization which includes the step of providing a chemical composition to be sterilized. The chemical composition is then charged into a container and the container is encased within a first sealing layer forming a single layer sealed container enclosure. The single layer sealed container enclosure is then encased within a second sealing layer forming a second layer sealed container enclosure. Both the first and second sealing layers provide for hermetic sealing and the entire second layer sealed container enclosure is inserted into a carton which is lined with a third sealing layer. The third sealing layer is then closed and the entire carton is irradiated at a predetermined radiation level for sterilizing the chemical composition contained within the original container.

DESCRIPTION OF THE PREFERRED EMBODIMENTS

Referring now to FIGS. 1–5, there is shown a method of sterilization for maintaining chemical compositions in a sterilized state over an extended period of time. The subject invention concept is directed to both the combined sterilization process for chemical compositions in combination with the maintenance of the sterilization state for the chemical compositions over a long period of time in order that the user may safely use the sterilized compositions at their discretion with the assurance that the chemical composition remains in a sterilized state. Thus, the problems associated with sterilization are two-fold in nature where the initial problem of sterilization is only one portion of the maintenance of the sterilization concept of the subject method. In general, chemical compositions are sterilized and then shipped in cartons such as cardboard containers with a plastic lining to protect the sterilized compositions maintained in their own containers within the cardboard cartons. The cardboard cartons are generally shipped by normal shipping procedures such as trucks, rail cars, or air transportation. The cartons are brought to the site where the sterilized containers are to be used and in general, procedures have been worked out where the containers and their plastic enclosure are brought internal to the work place while the container which may by then have various contaminating microbes or other particulates are left external to the workplace. The workplace then may store the chemical composition containers in a clean room or other type of room which in itself is designated as a room relatively free of contaminants but such clean rooms also have microbes and various other contaminating particulates in the atmosphere. Thus, a shelf life must be designated for such sterilized chemical composition containers even when used in a clean room type of atmosphere.

In order to solve the problem of shelf life, the subject invention concept's method provides for a series of steps which allow the sterilized chemical compositions within their own containers to be maintained over extended periods of time without a shelf life dependent on the sterilized state being designated nor being important to the maintenance of the chemical composition sterilization.

The use of the subject invention concept method for sterilization of chemical compositions has great use in the pharmaceutical industry. The pharmaceutical industry uses a large amount of alcohol for decontamination since it does kill various organisms. Thus, the pharmaceutical industry demands sterile alcohol and in particular the chemical compositions as herein described and detailed direct themselves to alcohol compositions and particularly to isopropyl alcohol used extensively in the pharmaceutical industry.

Figure 1:
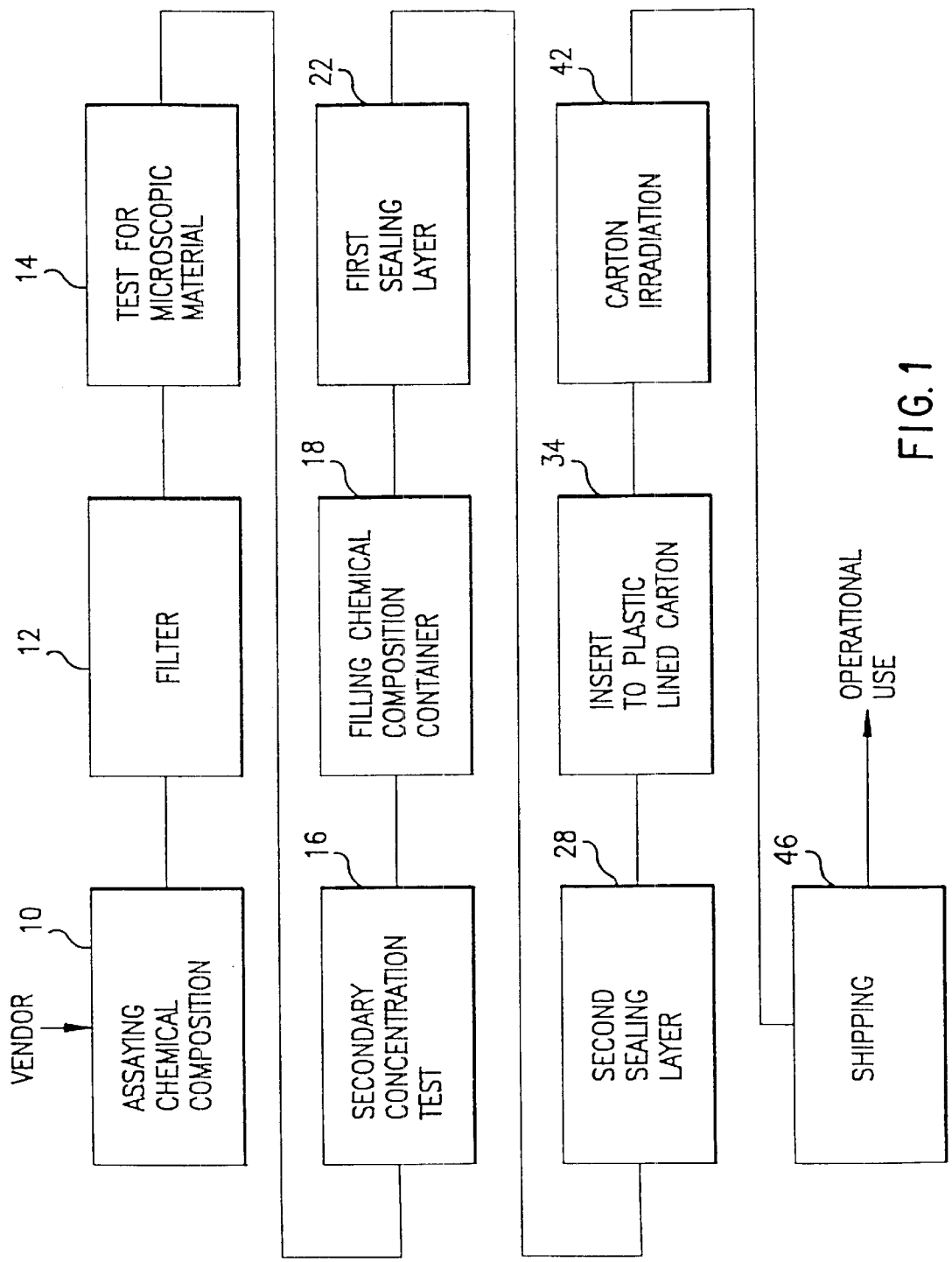
FIG. 1 is a block diagram showing the method steps for the method of sterilization as herein described.

Referring now to FIG. 1 which provides a block diagram associated with the overall method of sterilization as herein described, the chemical composition is obtained from a vender and assayed in block 10 wherein it is determined that a proper formulation of the chemical composition has been received. In the case of isopropyl alcohol many different types of composition formulations may be required under varying statutory laws associated with sterilization in different environments. In general, if an alcohol such as isopropyl alcohol is used it may be assayed or measured to provide predetermined compositions or formulations, two of the standards being 70% isopropyl alcohol with 30% water or 91% isopropyl alcohol and 9% water by volume.

The analyzed and measured chemical composition is then passed to a filter mechanism represented by block 20 in FIG. 1. The filter shown in block 12 may be a standard mechanical filter such as a cartridge filter having a predetermined filtering range such as a 0.22 micron filter to allow removal of particulate matter greater than the filter size. In effect, filter 12 removes residual particulates that may be in the chemical composition and at the size range of 0.22 microns even removes bacteria that may be in the chemical composition liquid. Thus, certain bacteria and spores as well as other particulate contaminants are removed during this phase of the overall method of sterilization.

The chemical composition is brought from the mechanical filter 12 to block 14 which is a test for particulate or microscopic matter. Testing is done in accordance with Test Number 788 dictated in the USP XXII Journal for determination of particulate matter contained within various chemical compositions. The test procedure is well known and used as a standard in the chemical industry where the composition is mixed in a container and the chemical composition has a vacuum applied thereto to allow passage into and through a filter. A section of the filter assembly is removed from the container while maintaining the vacuum and the filter is then placed in a Petri slide. The filter is dried with the cover of the Petri slide slightly open and particles on the filter are counted. Such testing is well known in the art and determines whether particulate matter of predetermined sizes has been removed from the chemical composition.

Once the particulate material testing in block 14 has been completed, the chemical composition is then brought to a secondary concentration test block 16 where the concentration of the chemical composition is once again analyzed to make sure that the proper chemical composition formulation has teen maintained. Secondary concentration test block 16 may be a standard well known concentration test as was provided in block 10. Once the chemical composition has passed through secondary concentration test block system 16, the chemical composition is then ready for packaging and has been assured of a proper formulation composition as well as an assurance to the fact that predetermined particulate sizes have been removed from the overall chemical composition.

Thus, in the flow blocks associated with FIG. 1, after passage through the initial concentration or assaying test block 10, mechanical filter 12, testing for microscopic material 14 and insertion into the secondary concentration test block 16, there has been provided a chemical composition of predetermined concentration which is to be sterilized in accordance with the invention concept steps of the subject method.

Figure 2:
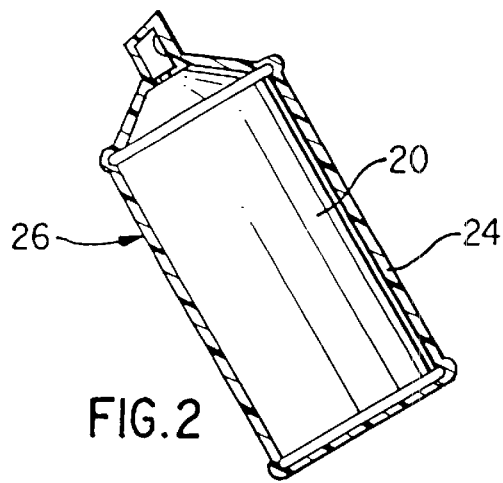
FIG. 2 is a cross-sectional view of a first sealing layer being placed over a chemical container.
Figure 3:
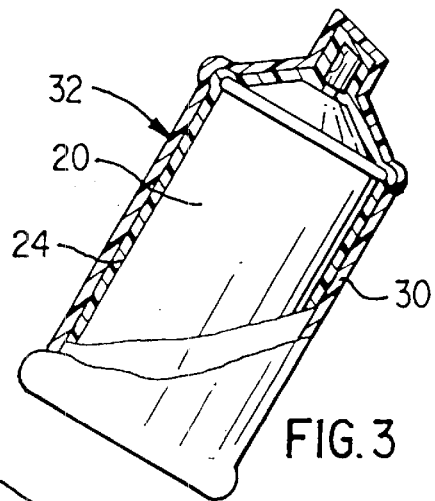
FIG. 3 is a cross-sectional view of a second sealing layer encasing the first sealing layer and forming a second layer sealed container enclosure.

After the secondary concentration testing as shown in block 16 is completed, container 20 shown in FIGS. 2 and 3 is filled with the chemical composition as provided in block 18 of FIG. 1. Chemical composition container 20 may be a standard aerosol can or alternatively may be a container with a cap closure. When using isopropyl alcohol as the chemical composition, such is generally inserted under pressure with an inert element such as nitrogen or another chemical formulation acting as the propellant into an aerosol can type chemical composition container 20. Once the chemical composition is inserted into chemical composition container 20 as shown in block 18, a nozzle may be mounted at one end with differing nozzle pattern generating systems being used dependent upon what is necessary for a particular decontamination operation. Such type of closure whether it be a nozzle arrangement system or a cap closure is not important to the inventive concept as herein described with the exception that such provide egress of the chemical composition appropriate for a particular decontamination operation. Once the filling composition container 20 has been filled, the operational phase moves to block diagram 22 of FIG. 1 where container 20 is encased within first sealing layer 24 forming a single layer sealed container enclosure 26.

First layer 24 seen in FIGS. 2 and 3, may be formed of a plastic composition of the closed cell type and in particular may be formed of a polyethylene composition. Once chemical composition container 20 has been encased by first layer 24, first layer 24 may be heat sealed to form a substantially hermetic seal for chemical composition container 20 as shown in FIG. 2. At this stage of the process steps, single layer sealed enclosure 26 has been created and is moved to block 28 of FIG. 1 where second sealing layer 30 encases single layer sealed enclosure 26 to form second layer sealed container enclosure 32. Second sealing layer 30 may also be formed of a plastic composition of the closed cell type and in particular may also be a polyethylene composition similar to first layer 24. Second sealing layer 30 may then be also heat sealed to provide a hermetically sealed second layer sealed container enclosure 32 as shown in FIG. 3.

Figure 4:
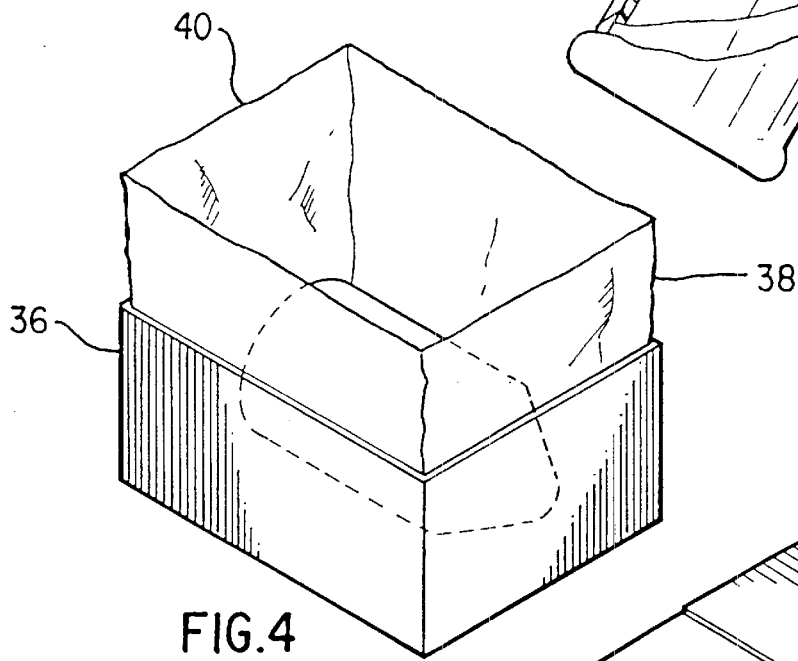
FIG. 4 is a cross-sectional view of a carton having a third sealing layer lining for insertion of the second layer sealed container enclosure; and, FIG. 5 is a perspective view of a closed carton member being irradiated in a plurality of planes.

Once second sealing layer 30 has been applied and heat sealed to establish second layer sealed container enclosure 32., the enclosure 32 is then inserted into plastic lined carton 36 as shown in FIG. 4 and depicted in flow block 34 of FIG. 1. Carton 36 may be a cardboard type container adaptable for transportation and associated shipping to the operations site. Additionally, there is provided third sealing layer 38 as shown in FIG. 4, which is a lining for carton 36. Third sealing layer 38 may once again be formed of a plastic type composition of the closed cell type which may also be a polyethylene bag-like element. Third sealing layer 38 lines the internal walls of carton 36 in order to provide an insert for one or a plurality of second layer sealed container enclosures 32 therein. Third sealing layer 38 may then be closed through tying or some like closure mechanism at an upper section 40 and in this manner the entire second layer sealed container enclosure 32 is then contained therein. Finally, carton 36 may be closed in the standard manner of flap closures for container members.

Figure 5:
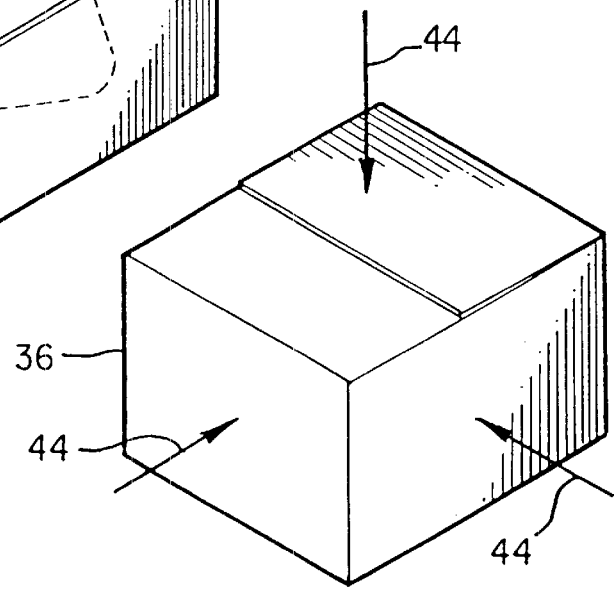

Once the second layer sealed container enclosure has been inserted into lined carton 36 as shown in block 34 of FIG. 1, carton 36 is then brought to block 42 for carton irradiation processes. The carton irradiation step as depicted in block 42 of FIG. 1 may be a gamma irradiation system where the decay of each atom of cobalt 60 generates a pair of photons of gamma radiation having predetermined energies as well as a beta particle. The beta particle is captured within a housing of the cobalt 60 and the photons of gamma radiation provide for the sterilization radiation process. In general, cartons 36 are brought into the irradiation plant where the cobalt 60 is transported in shielded flasks. Following transfer from the flasks to the irradiation plant, doubly encapsulated cobalt 60 in stainless steel tubes are incorporated into a three-dimensional array which form the energy source for processing carton 36 as depicted in FIG. 5 where the directional arrows 44 show impingement of the gamma radiation in a three-dimensional array direction concept. Cartons 36 are generally passed through the irradiation plant on conveyor systems either using roller beds or suspended carrier systems where the gamma radiation dose absorbed by the chemical composition within the closed cartons 36 is directly proportional to the activity level of the source and the duration of exposure.

Gamma radiation is generally used for sterilization of chemical compositions in that the gamma radiation has a high penetration capability. This high penetration capability enables relatively dense products or compositions to be processed easily. Dosages are generally defined in Grays with one Gray representing the absorption of one Joule of energy per kilogram of material. Sterilizing doses generally are in the 25–35 kilogray range and as the products undergo the irradiation process, obviously the face of carton 36 facing the source of radiation will receive a higher dosage than the side away from the source.

To insure appropriate dose levels between 20–40 kilograys, carton 36 is measured with dosimeters which measure the amount of irradiation impinging on the closed carton 36. In this manner, the contents of container 20 is assured of appropriate irradiation levels being applied thereto.

The closed cartons 36 are then prepared for shipping as provided in block 44 of FIG. 1 and are transported for operational use downstream.

In this manner, when received at the operational site, closed cartons 36 may be then opened and third sealing layer 38 contained therein may be removed on the loading dock prior to entry into a clean room. The chemical containers 20 are maintained within third sealing layer 38 in a closed manner until removed and then brought to a clean room type operating site with the opened container 36 being left on the loading dock.

Once transported into the clean room or other operational site, third sealing layer 38 may be removed and the chemical containers 20 forming second layer sealed container enclosures 32 may be placed on a shelf for future use. It must be remembered that at this point, there is both a first layer 24 and a second sealing layer 30 encompassing chemical container 20. When placing the second layer sealed container enclosures 32 on the shelves for use in the clean rooms, generally sterilized gloves are used however, these in themselves as well as the atmosphere of clean rooms have various particulates such as microbes or bacteria which dictate a shelf life for chemical containers 20 if only a single first layer 24 were formed around the chemical containers 20. However, with the first and second layers 24 and 30, the now somewhat less than sterilized second layer sealed container enclosure 32 may be kept on the shelf for an indefinite period of time prior to use of the contents of chemical container 20.

Once the contents of chemical container 20 are to be used, second sealing layer 30 may be stripped from second layer sealed container enclosure 32 leaving first layer 24 surrounding and encasing chemical container 20 in a sterilized manner. Use then can be made of the contents of chemical containers 20 with the assurance that such has been maintained in a sterilized state.

Thus, there has been shown a method of sterilization for chemical compositions in general and in particular isopropyl alcohol compositions where the chemical composition to be sterilized is provided prior to block 10. In overall concept the chemical composition is secondarily tested for its appropriate concentration in block 16 with an additional test for particulate or microscopic material being made in block 14. A container 20 is then charged with the chemical composition as provided in block 18 and container 20 is encased within first sealing layer 24 forming a single layer sealed container enclosure 26 as provided in block 22.

After the first sealing layer 24 is applied, the single layer sealed container enclosure 26 is then encased within second sealing layer 30 forming a second layer sealed container enclosure 32 as provided in flow block 28. The encasement is provided for hermetically sealing initially the chemical container 20 with the first layer 24 and then the single layer sealed enclosure 26 with the second sealing layer 30 as shown in FIGS. 2 and 3.

The second layer sealed container enclosure 32 is then inserted into an open carton member 36 which is lined with a third sealing layer 38 as shown in flow block 34 and depicted in FIG. 4. The carton member is then closed as depicted in FIG. 5 and irradiated at a predetermined radiation level for some predetermined time interval for sterilizing the chemical composition contained within container 20.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

I claim:

1. A method of sterilizing a chemical composition contained in a sealed container comprising the steps of, under non-sterile conditions:

providing a container having an internal volume;

charging the internal volume of the container with a quantity of chemical composition;

sealing the internal volume of the container to form a sealed container;

hermetically heat sealing the container in a first sealing layer to form a first hermetically heat-sealed container enclosure;

hermetically heat sealing said first hermetically sealed container enclosure in a second sealing layer to form a second hermetically heat-sealed container enclosure;

enclosing said second hermetically heat-sealed container enclosure in a shipping carton to form a closed shipping package the contents of which include said chemical composition, said sealed container, and said first and second hermetically heat-sealed container enclosures;

transferring said closed shipping package with its contents in a non-sterile condition to an irradiation plant; and externally irradiating said closed shipping package and its contents at the irradiation plant at a predetermined radiation level for a predetermined time interval to simultaneously sterilize said chemical composition, said sealed container, and said first and second hermetically heat-sealed container enclosures.

2. The method of claim 1 comprising enclosing a plurality of said second hermetically heat-sealed container enclosures in each of a plurality of said shipping cartons to form a plurality of closed shipping packages, transferring said plurality of closed shipping packages and their contents in a non-sterile condition to an irradiation plant, and externally irradiating said closed shipping packages and their contents at the irradiation plant at a predetermined radiation level for a predetermined time interval to simultaneously sterilize the chemical compositions, the sealed containers, and the first and second hermetically heat-sealed container enclosures contained in each closed shipping package.

3. The method of claim 2 wherein each container is an aerosol container and including the step of pressurizing the internal volume of each aerosol container with an inert gas prior to sealing each container.

4. The method of claim 1 wherein said first and second sealing layers each consist of a single layer of a polyethylene plastic material.

5. A method of storing a sterilized chemical composition and maintaining the sterilization shelf life of the sterilized chemical composition for a prolonged period of time, said sterilized chemical composition being contained in a plurality of sealed containers, each sealed container being hermetically sealed in a first hermetically sealed container enclosure, each first hermetically sealed container enclosure containing a sealed container being hermetically sealed in a second hermetically sealed container enclosure, a plurality of the second hermetically sealed container enclosures each containing a first hermetically sealed container enclosure and a sealed container being enclosed in a shipping enclosure to form a closed shipping package the contents of which have been sterilized by radiation at an irradiation plant and transported to a storage area for operational use, comprising the steps of:

opening the closed shipping package and removing the sterilized second hermetically sealed container enclosures each containing a sterilized sealed container and a sterilized first hermetically sealed container enclosure from the closed shipping package;

storing the sterilized second hermetically sealed container enclosures each containing a sterilized sealed container and a sterilized first hermetically sealed container enclosure in the storage area for a period of time;

after the period of time, removing at least one of the sterilized second hermetically sealed container enclosures from the storage area, opening the removed second hermetically sealed container enclosure and transporting the sterilized first hermetically sealed container enclosure containing the sterilized sealed container to a sterile environment; and opening the sterilized first hermetically sealed container enclosure in the sterile environment and removing the sterilized sealed container from the sterilized first hermetically sealed container enclosure for use of the sterilized chemical composition in the sterile environment.

6. A closed shipping package adapted to be terminally sterilized with radiation comprising a plurality of non-sterile, sealed aerosol containers each having an internal volume and being charged with a quantity of a chemical composition and pressurized with an inert gas, a non-sterile first hermetically sealed container enclosure hermetically sealing each aerosol container, a non-sterile second hermetically sealed container enclosure hermetically sealing each first hermetically sealed container enclosure, each non-sterile second hermetically sealed container enclosure containing a non-sterile, sealed aerosol container contained within a non-sterile first hermetically sealed container enclosure, and a shipping carton enclosing a plurality of the non-sterile second hermetically sealed container enclosures to form a non-sterile closed shipping package, the non-sterile closed shipping package externally radiated at a predetermined radiation level for a predetermined time interval to simultaneously sterilize the chemical compositions, the non-sterile, sealed aerosol containers and the non-sterile first and second hermetically sealed container enclosures.

7. The closed shipping package of claim 6 wherein said chemical composition is alcohol and said first and second hermetically sealed container enclosures consist of a single layer of a polyethylene plastic material.

* * * * *

(12) EX PARTE REEXAMINATION CERTIFICATE (9098th)
United States Patent
Vellutato

(10) Number: US 6,607,695 C1
(45) Certificate Issued: *Jun. 26, 2012

(54) METHOD OF STERILIZATION

(76) Inventor: Arthur L. Vellutato, Exton, PA (US)

Reexamination Request:
No. 90/009,290, Oct. 1, 2008

Reexamination Certificate for:
Patent No.: 6,607,695
Issued: Aug. 19, 2003
Appl. No.: 09/994,671
Filed: Nov. 28, 2001

( * ) Notice: This patent is subject to a terminal disclaimer.

Related U.S. Application Data

(63) Continuation of application No. 09/627,398, filed on Jul. 27, 2000, now Pat. No. 6,333,006, which is a continuation of application No. 08/142,049, filed on Oct. 28, 1993, now Pat. No. 6,123,900.

(51) Int. Cl.
*A61L 2/00* (2006.01)
*A61L 2/08* (2006.01)

(52) U.S. Cl. .............. 422/22; 422/40; 250/455.11
(58) Field of Classification Search .............. None
See application file for complete search history.

(56) References Cited

To view the complete listing of prior art documents cited during the proceeding for Reexamination Control Number 90/009,290, please refer to the USPTO's public Patent Application Information Retrieval (PAIR) system under the Display References tab.

*Primary Examiner* — Krisanne Jastrzab

(57) ABSTRACT

A sterilized chemical composition is stored in a sterile environment for a prolonged period of time, hermetically sealed in successive enclosures and a shipping enclosure. The third sealing layer is removed prior to entering a storage area. The second layer is removed prior to taking the container to the sterile environment. The storage area may also be sterile. The innermost container may be an aerosol container and the composition a disinfectant liquid such as alcohol. The entire shipping enclosure and contects is preferably sterilized with gamma radiation.

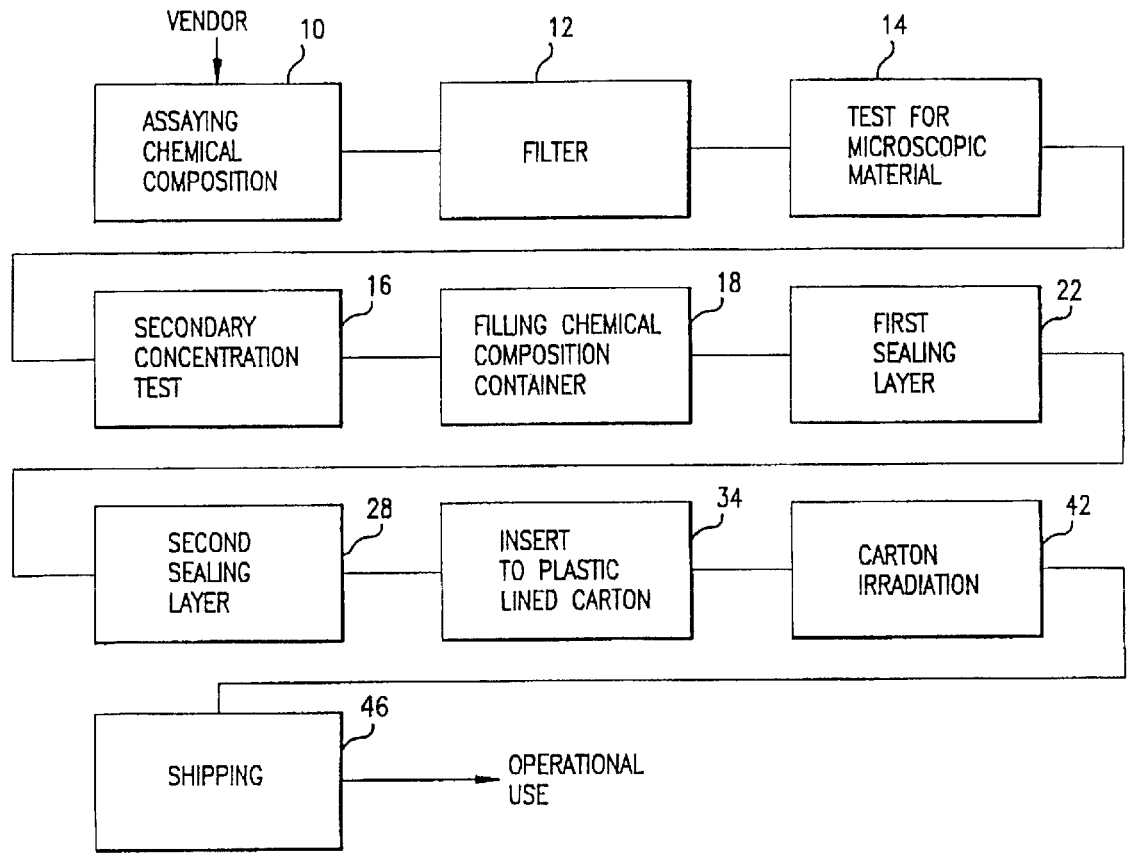

US 6,607,695 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 6-7 are cancelled.

Claims 1-2 are determined to be patentable as amended.

Claims 3-4 dependent on an amended claim, are determined to be patentable.

New claims 8-43 are added and determined to be patentable.

Claim 5 was not reexamined.

1. A method of sterilizing, *under non-sterile conditions,* a chemical [composition] *disinfectant* contained in a sealed container comprising the steps of[, under non-sterile conditions]:
   providing a container having an internal volume;
   charging the internal volume of the container with a quantity of *said* chemical [composition] *disinfectant suitable for being discharged under pressure from said container and effective for use in a decontamination procedure in a controlled environment;*
   *pressurizing the internal volume of the container;*
   sealing the internal volume of the container to form a sealed container;
   hermetically heat sealing the container in a first sealing layer to form a first hermetically heat-sealed container enclosure;
   hermetically heat sealing said first hermetically sealed container enclosure in a second sealing layer to form a second hermetically heat-sealed container enclosure;
   enclosing said second hermetically heat-sealed container enclosure in a shipping carton to form a closed shipping package the contents of which include said chemical [composition] *disinfectant*, said sealed container, and said first and second hermetically heat-sealed container enclosures;
   transferring said closed shipping package with its contents in a non-sterile condition to an irradiation plant; and
   externally irradiating said closed shipping package and its contents at the irradiation plant at a predetermined radiation level for a predetermined time interval to simultaneously sterilize said chemical [composition] *disinfectant*, said sealed container, and said first and second hermetically heat-sealed container enclosures, *said radiation level and time interval being controlled so as to retain the effectiveness of said chemical disinfectant.*

2. The method of claim 1 comprising enclosing a plurality of said second hermetically heat-sealed container enclosures in each of a plurality of said shipping cartons to form a plurality of closed shipping packages, transferring said plurality of closed shipping packages and their contents in a non-sterile condition to an irradiation plant, and externally irradiating said closed shipping packages and their contents at the irradiation plant at a predetermined radiation level for a predetermined time interval to simultaneously sterilize the chemical [compositions] *disinfectant*, the sealed containers, and the first and second hermetically heat-sealed container enclosures contained in each closed shipping package.

8. *A method of sterilizing, under non-sterile conditions, alcohol contained in a sealed container comprising the steps of:*
   *providing a container having an internal volume;*
   *charging the internal volume of the container with a quantity of alcohol for being discharged from said container and for use in a decontamination procedure in a clean room, wherein the alcohol comprises a chemical disinfectant;*
   *pressurizing the internal volume of said container with an inert gas;*
   *sealing the internal volume of the container to form a sealed container;*
   *hermetically heat sealing the container in a first sealing layer to form a first hermetically heat-sealed container enclosure;*
   *hermetically heat sealing said first hermetically sealed container enclosure in a second sealing layer to form a second hermetically heat-sealed container enclosure;*
   *enclosing said second hermetically heat-sealed container enclosure in a shipping carton to form a closed shipping package the contents of which include said alcohol, said sealed container, and said first and second hermetically heat-sealed container enclosures;*
   *transferring said closed shipping package with its contents in a non-sterile condition to an irradiation plant; and*
   *externally irradiating said closed shipping package and its contents at the irradiation plant at a predetermined radiation level for a predetermined time interval to simultaneously sterilize said alcohol, said sealed container, and said first and second hermetically heat-sealed container enclosures, wherein said alcohol is suitable for the decontamination procedure following said step of externally irradiating, and whereby said sealed container can be introduced into the clean room and said alcohol can be discharged under pressure from said sealed container in the clean room.*

9. *The method of claim 8 wherein each container is an aerosol container.*

10. *The method of claim 8 wherein said externally irradiating comprises subjecting said closed shipping package and its contents to gamma radiation.*

11. *The method of claim 8, wherein said alcohol is isopropyl alcohol.*

12. *A method of sterilizing, under non-sterile conditions, alcohol contained in a sealed aerosol container comprising the steps of:*
   *providing an aerosol container having an internal volume;*
   *filtering the alcohol to provide a filtered alcohol which is for use in a decontamination procedure in a controlled environment, wherein the alcohol comprises a chemical disinfectant;*
   *charging the internal volume of the aerosol container with a quantity of the filtered alcohol for being discharged* under pressure from said aerosol container and for use in the decontamination procedure in the controlled environment;

pressurizing the internal volume of the aerosol container;

sealing the internal volume of the aerosol container to form a sealed container;

hermetically heat sealing the aerosol container in a first sealing layer to form a first hermetically heat-sealed container enclosure;

hermetically heat sealing said first hermetically sealed container enclosure in a second sealing layer to form a second hermetically heat-sealed container enclosure;

enclosing said second hermetically heat-sealed container enclosure in a shipping carton to form a closed shipping package the contents of which include said alcohol, said sealed aerosol container, and said first and second hermetically heat-sealed container enclosures;

transferring said closed shipping package with its contents in a non-sterile condition to an irradiation plant; and externally irradiating said closed shipping package and its contents at the irradiation plant at a predetermined radiation level for a predetermined time interval to simultaneously sterilize said alcohol, said sealed aerosol container, and said first and second hermetically heat-sealed container enclosures, and to retain effectiveness of said alcohol in the decontamination procedure.

13. *The method of claim 12 wherein said externally irradiating comprises subjecting said closed shipping package and its contents to gamma radiation.*

14. *The method of claim 12, wherein said alcohol is isopropyl alcohol.*

15. *The method of claim 12, wherein said pressuring comprises pressurizing the internal volume of the aerosol container with an inert gas.*

16. *The method of claim 1, further comprising the step of filtering the chemical disinfectant prior to said step of charging.*

17. *The method of claim 16, wherein said step of filtering comprises filtering the chemical disinfectant with a 0.22 micron filter.*

18. *The method of claim 1, wherein the chemical disinfectant is suitable for the decontamination procedure following said step of externally irradiating.*

19. *The method of claim 1, wherein the container has a nozzle and the chemical disinfectant can be discharged from the container through the nozzle.*

20. *The method of claim 1, wherein said chemical disinfectant consists essentially of at least 70% isopropyl alcohol with a remainder of water by volume.*

21. *The method of claim 1, wherein said controlled environment comprises a clean room.*

22. *The method of claim 1, wherein said chemical disinfectant consists essentially of 70% isopropyl alcohol and 30% water by volume.*

23. *The method of claim 12, wherein said controlled environment comprises a clean room.*

24. *The method of claim 1, wherein said chemical disinfectant consists essentially of at least 91% isopropyl alcohol with a reminder of water by volume.*

25. *The method of claim 1, wherein said irradiating step comprises subjecting the closed shipping package to gamma radiation in the range of about 20 to 40 kilograys.*

26. *The method of claim 1, wherein said irradiating step comprises subjecting the closed shipping package to gamma radiation in the range of about 25 to 35 kilograys.*

27. *The method of claim 1, wherein said pressurizing comprises pressurizing the internal volume of the container with an inert gas.*

28. *The method of claim 1, wherein said pressurizing comprises pressurizing the internal volume of the container with nitrogen.*

29. *The method of claim 1, said container having an outside surface, and wherein said step of irradiating comprises simultaneously sterilizing said chemical disinfectant, said sealed container, said first and second hermetically heat-sealed container enclosures, and said outside surface of said container.*

30. *A method of sterilizing, under non-sterile conditions, a chemical disinfectant contained in a sealed container comprising the steps of:* providing a container having an internal volume;

charging the internal volume of the container with a quantity of said chemical disinfectant, said chemical disinfectant consisting essentially of isopropyl alcohol, wherein said isopropyl alcohol can be discharged under pressure from said container for use in a decontamination procedure in a controlled environment;

pressurizing the internal volume of the container;

sealing the internal volume of the container to form a sealed container;

hermetically heat sealing the container in a first sealing layer to form a first hermetically heat-sealed container enclosure;

hermetically heat sealing said first hermetically sealed container enclosure in a second sealing layer to form a second hermetically heat-sealed container enclosure;

enclosing said second hermetically heat-sealed container enclosure in a shipping carton to form a closed shipping package the contents of which include said isopropyl alcohol, said sealed container, and said first and second hermetically heat-sealed container enclosures;

transferring said closed shipping package with its contents in a non-sterile condition to an irradiation plant; and externally irradiating said closed shipping package and its contents at the irradiation plant at a predetermined radiation level for a predetermined time interval to simultaneously sterilize said isopropyl alcohol, said sealed container, and said first and second hermetically heat-sealed container enclosures, whereby said sealed container can be introduced into the controlled environment and said isopropyl alcohol can be discharged under pressure from said sealed container in the controlled environment.

31. *The method of claim 30, further comprising the step of filtering the chemical disinfectant prior to said step of charging.*

32. *The method of claim 31, wherein said step of filtering comprises filtering the chemical disinfectant with a 0.22 micron filter.*

33. *The method of claim 30, wherein the chemical disinfectant is suitable for the decontamination procedure following said step of externally irradiating.*

34. *The method of claim 30, wherein the container has a nozzle and the chemical disinfectant can be discharged from the container through the nozzle.*

35. *The method of claim 30, wherein said chemical disinfectant consists essentially of at least 70% isopropyl alcohol with a remainder of water by volume.*

36. *The method of claim 30, wherein said controlled environment comprises a clean room.*

37. The method of claim 30, wherein said chemical disinfectant consists essentially of 70% isopropyl alcohol and 30% water by volume.

38. The method of claim 30, wherein said chemical disinfectant consists essentially of at least 91% isopropyl alcohol with a reminder of water by volume.

39. The method of claim 30, wherein said irradiating step comprises subjecting the closed shipping package to gamma radiation in the range of about 20 to 40 kilograys.

40. The method of claim 30, wherein said irradiating step comprises subjecting the closed shipping package to gamma radiation in the range of about 25 to 35 kilograys.

41. The method of claim 30, wherein said pressurizing comprises pressurizing the internal volume of the container with an inert gas.

42. The method of claim 30, wherein said pressurizing comprises pressurizing the internal volume of the container with nitrogen.

43. The method of claim 30, said container having an outside surface, and wherein said step of irradiating includes simultaneously sterilizing said alcohol, said sealed container, said first and second hermetically heat-sealed container enclosures, and said outside surface of said container.

* * * * *